United States Patent
Hu et al.

(10) Patent No.: US 6,621,918 B1
(45) Date of Patent: Sep. 16, 2003

(54) TELERADIOLOGY SYSTEMS FOR RENDERING AND VISUALIZING REMOTELY-LOCATED VOLUME DATA SETS

(75) Inventors: Hui Hu, Waukwesha, WI (US); Jun Zhang, Shorewood, WI (US)

(73) Assignee: H Innovation, Inc., Wauwatosa, WI (US)

( * ) Notice: Subject to any disclaimer, the term of this patent is extended or adjusted under 35 U.S.C. 154(b) by 0 days.

(21) Appl. No.: 09/434,088

(22) Filed: Nov. 5, 1999

(51) Int. Cl.$^7$ .............................................. G06K 9/00
(52) U.S. Cl. ...................................... 382/128; 434/262
(58) Field of Search ......................... 382/100, 128–134, 382/206; 128/922, 904; 600/382; 221/7; 324/309, 323; 345/418, 700; 348/65, 77; 434/262

(56) References Cited

U.S. PATENT DOCUMENTS

| | | | | |
|---|---|---|---|---|
| 4,737,921 A | | 4/1988 | Goldwasser et al. | 345/421 |
| 4,748,511 A | | 5/1988 | Nichols et al. | 382/232 |
| 4,961,425 A | * | 10/1990 | Kennedy et al. | 600/425 |
| 5,235,510 A | * | 8/1993 | Yamada et al. | 128/922 |
| 5,291,401 A | | 3/1994 | Robinson | 382/132 |
| 5,432,871 A | | 7/1995 | Novik | 382/232 |
| 5,596,994 A | * | 1/1997 | Bro | 128/904 |
| 5,603,323 A | * | 2/1997 | Pflugrath et al. | 128/903 |
| 5,649,173 A | | 7/1997 | Lentz | 345/501 |
| 5,660,176 A | * | 8/1997 | Iliff | 600/300 |
| 5,715,823 A | * | 2/1998 | Wood et al. | 128/904 |
| 5,730,146 A | * | 3/1998 | Itil et al. | 600/382 |
| 5,836,877 A | * | 11/1998 | Zavislan | 128/922 |
| 6,283,322 B1 | * | 9/2001 | Liff et al. | 221/7 |
| 6,283,761 B1 | * | 9/2001 | Joao | 128/923 |
| 6,362,620 B1 | * | 3/2002 | Debbins et al. | 324/309 |
| 6,369,812 B1 | * | 4/2002 | Iyriboz et al. | 345/419 |
| 6,381,029 B1 | * | 4/2002 | Tipirneni | 358/1.14 |

OTHER PUBLICATIONS

"3D displays for computed tomography", by Sandy Napel p 603–626, in the book entitled "Medical CT and Ultrasound: current technology and applications" published by Advanced Medical Publishing, 1995.

"Data and Visualization Corridors: Report on the 1998 DVC Workshop Series" by P.H. Smith & J. van Rosendale, California Institute of Technology Technical Report CACR—164 Sep. 1998.

* cited by examiner

*Primary Examiner*—Jayanti K. Patel
(74) *Attorney, Agent, or Firm*—Morrison & Foerster LLP

(57) ABSTRACT

A teleradiology system provides the capability of rendering and studying of a remotely located volume data without requiring transmission of the entire data to the user's local computer. The system comprises: receiving station (300) under the control of a user (400); transmitting station (100); the connecting network (200); the user interface (32) with functionality of controlling volume data rendering, transmission, and display; and the interface with patient data source (10). The teleradiology system of the invention provides an integrated functionality of data transmission of current teleradiology systems and volume data rendering/visualization of current volume data rendering/visualization systems. The system may be readily used with an intranet, the internet (including the internet2) or via a direct dial-up using a telephone line with a modem, and can serve as an enterprise-wide PACS and may be readily integrated with other PACS and image distribution systems. Software of this system can be centrally installed and managed and can be provided to the user's local computer on an as-needed basis. Furthermore, the software for the user's computer is developed to use with standard web browser. This system provides a secure, cost-effective, widely-accessible solution for data rendering and visualization. It provides a suitable image distribution method for medical image data, for medical data repository, and for the electronic medical record (or the computerized patient record). It allows healthcare providers (e.g., radiologists, other physicians, and supporting staffs) to render and study remotely located patient data at the locations of their choices.

20 Claims, 2 Drawing Sheets teleradiology system
with remote volume data rendering / visualization capability

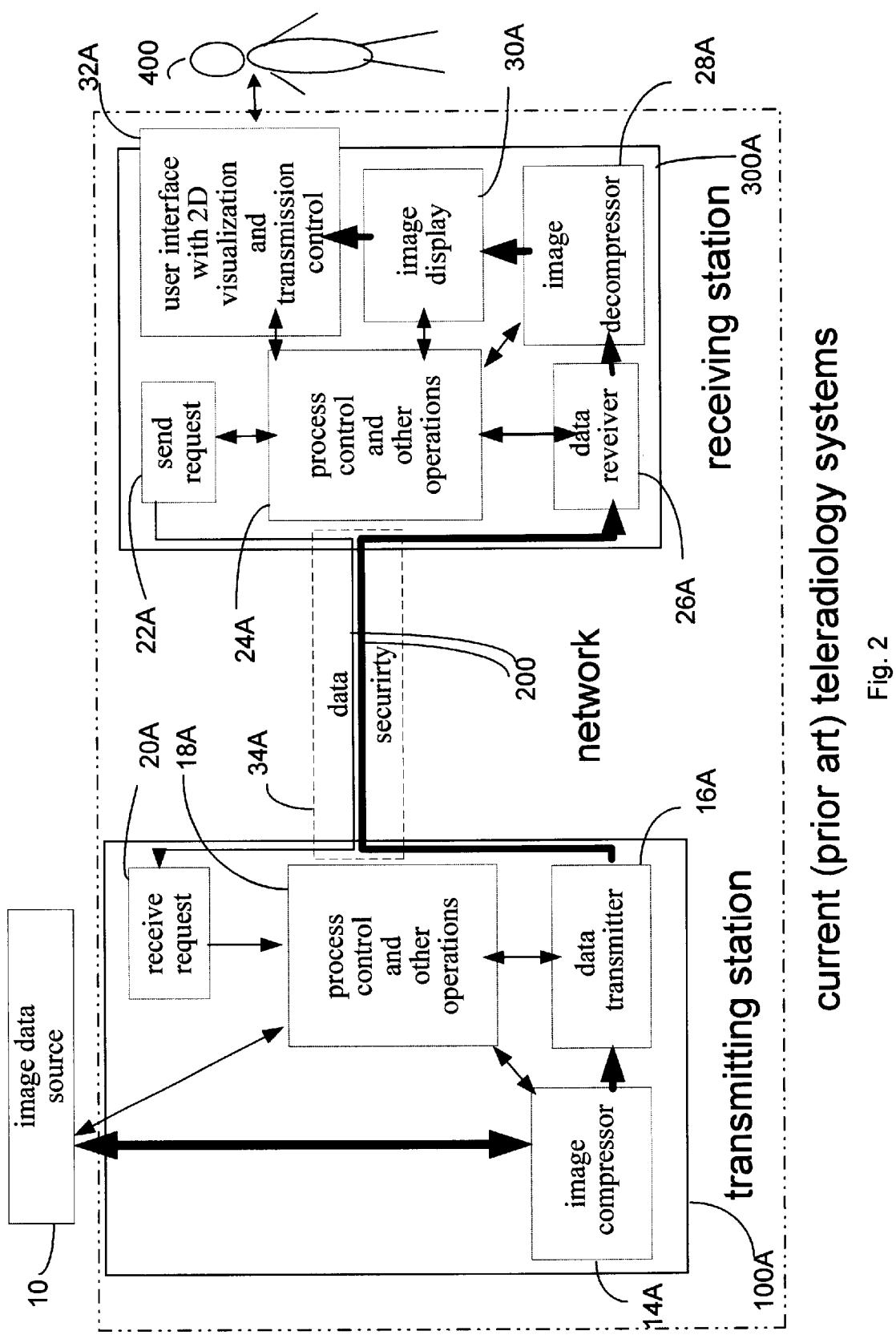
Fig. 2 current (prior art) teleradiology systems

TELERADIOLOGY SYSTEMS FOR RENDERING AND VISUALIZING REMOTELY-LOCATED VOLUME DATA SETS

BACKGROUND OF THE INVENTION

The present invention generally relates to teleradiology systems, specifically to teleradiology systems with remote volume data rendering and visualization capability.

Teleradiology is a means of electronically transmitting radiographic patient images and consultative text from one location to another. Teleradiology systems have been widely used by healthcare providers to expand the geographic and/or time coverage of their service, thereby achieving efficiency and utilization of healthcare professionals (e.g., radiologists) with specialty and subspecialty training and skills, resulting in improved healthcare service quality, delivery time, and reduced cost.

Existing teleradiology systems have been designed for, and are only capable of, transmitting two-dimensional (2D) images in a predetermined order, similar to a fax machine, faxing page by page in a predetermined order. Prior art includes U.S. Pat. No. 4,748,511 by Nichols et al, U.S. Pat. No. 5,291,401 by Robinson, and many related patents. None of them is optimized for volume data rendering and study.

Data rendering refers to the process of converting data into visual forms so that the information in the data can be understood and interpreted. These visual forms are usually shown on a two-dimensional monitor, film or even paper. Data visualization refers to the process of displaying and studying the rendering results. Two-dimensional data rendering and visualization is straightforward, as a 2D (M×N) data array can be readily presented as a 2D (M×N) image which can be displayed (e.g., on a monitor) or printed (e.g., on a film or paper). However, visualizing data of more than two-dimensions is a much more complex task. We refer to a data set with more than two dimensions as volume data.

Visualizing volume data requires volume data rendering methods. In general, a volume data rendering method reduces or converts an original volume data set into a synthesized data set of different forms, i.e., with reduced dimensions and with different data attributes. For example, one method of 3D volume data rendering is called Multi-Planer Reformation (MPR), which is derived from the data within a slice of the 3D data "cube" by averaging the data along the direction perpendicular to the slice. In this way, MPR reduces 3D data into a 2D image, presenting averaged data values in the slice. As the rendering parameters (e.g., the locations, orientations, and thickness of the slice) change, different 2D images (averaged data values) of the 3D dataset are obtained. With MPR, one can view images of any oblique slice in addition to conventional horizontal slices. Another method of volume data rendering is called Maximum Intensity Projection (MIP), where the intensity of each pixel in the MIP image is the maximum intensity encountered in the 3D dataset along each of the parallel or divergent paths defined by viewpoint. Besides MPR and MIP, volume data rendering methods of medical interest also include surface rendering and volume rendering, as well as many variations and/or combinations of these methods. For technical details of these data rendering methods, reference may be made to the review article, "3D displays for computed tomography", by Sandy Napel, p. 603–626, in the book entitled "Medical CT and Ultrasound: current technology and applications" published by Advanced Medical Publishing, 1995.

Medical image acquisition techniques include X-ray, Computed Tomography (CT), Magnetic Resonance (MR), UltraSound (US), and Nuclear Medicine. Nuclear Medicine further includes Single Photon Emission Computed Tomography (SPECT) and Position Emission Tomography (PET).

In modem medical diagnosis and treatment planning, acquisition of volume data becomes a rule rather than an exception. Thus, volume data rendering and visualization methods have become essential methods, in addition to the traditional slice-by-slice 2D image studies. For example, the de facto standard for CT angiography image display is MIP, which results in a 2D image highlighting the vascular structures. The volume data rendering result is usually obtained by interactively adjusting the rendering parameters, such as the viewpoint (i.e., the orientation), the spatial region and/or the value range of interest of the volume data.

There are many volume data rendering/visualization systems (including software and hardware). Prior art includes U.S. Pat. 4,737,921 by Goldwasser et al., U.S Pat. No. 5,649,173 by Lentz, and many related patents. In order to improve the graphics performance, the current volume data rendering/visualization systems have been designed as local dedicated systems, rather than as network based systems.

Currently, volume data rendering and visualization can only be done when the data to be rendered as well as the required rendering/visualization software and hardware are resided in the computer which is used to perform this task. If a user wants to obtain the volume data rendering result for a remotely located data set, he/she has to 1) transmit the entire volume data set from the remote location to his local computer via a network; 2) generate the rendering result from the local copy of the data and display the result, using the rendering/visualization software and hardware installed on his local computer. This approach, referred to as the two-step (i.e., transmitting and rendering/visualizing) approach, is often impractical and undesirable for the following reasons:

1) This approach requires transmitting a large volume data set (e.g., 150 MB in a CT angiography study) over a network, which frequently is not practical for even normal networks (such as, the Ethernet) available in a hospital setting. It is even less practical for a direct dial-up (from home) using a telephone line with a modem.
2) This approach causes a long initial delay because it takes a long time to transmit a large data set over a network, and the rendering and study cannot be started until transmission of the entire data set is completed. This delays the delivery of healthcare service.
3) This approach is costly because performing volume data rendering/visualization this way imposes stringent requirements on the network as well as the hardware (e.g., memory, storage, and processing power) and software (special for volume data rendering/visualization) of the user's local computer.
4) This approach, because of the high cost, cannot be deployed in a large scale, and therefore cannot serve as a healthcare enterprise-wide image distribution solution.
5) This approach cannot provide ubiquitous access and distribution of images to the points of the user's choice, as it can only provide image access via limited designated points of access.
6) Medical images are not used in a vacuum. Clinicians integrate the information derived from imaging studies with other clinical data (such as ECG, the blood pressure, the patient medical history) in order to make patient management decisions. What the clinician requires is ubiquitous access of the so-called electronic medical record, which integrates both image data and other clinical data. The two-step approach, due to its high cost and limited fixed access points, is not a suitable image distribution method for the electronic medical record.

7) This approach requires generating local copies of the patient data to be studied, which is often undesirable for patient data management.

Though solving above problems has substantial commercial benefits, no satisfactory solution exists that allows healthcare providers to render and study remotely located volume patient data.

Rendering and visualizing data generated by a remotely located scientific instrument or supercomputer has been studied for several years. Prior art includes U.S. Pat No. 5,432,871 by Novik and many related patents. Also reference may be made to "Data and Visualization Corridors: Report on the 1998 DVC Workshop Series" by P. H. Smith & J. van Rosendale, California Institute of Technology Technical Report CACR—164 September 1998. The applications taught hereby distinctly differ from teleradiology applications in the following aspects. 1) The objects to be studied are fundamentally different—patient data versus scientific measurements and computations, requiring different rendering/visualization methods as well as different user interactions/interfaces. 2) Teleradiology applications have unique requirements in regard to real-time interactivity and image fidelity. 3) Teleradiology applications require unique attentions to data security (including patient privacy) and data integrity as well as other medical and legal issues. 4) Teleradiology applications require a unique image distribution solution for medical image data and the electronic medical record that is suitable for large scale (e.g., healthcare enterprise-wide) deployment and that is fully integrated with medical image data source and data management.

SUMMARY OF THE INVENTION

This invention provides a method and apparatus that allow healthcare providers (e.g., radiologists, other physicians, and supporting staffs) to render and study remotely located volume patient data at the locations of their choices. The capability of rendering/visualizing remotely located volume data only becomes available by fully integrating data transmission and volume data rendering functionalities currently supported by two types of products, i.e., teleradiology systems and volume data rendering/visualization systems.

Objects and Advantages of the Invention

An object of the invention is to develop methods and apparatus that allow healthcare providers (e.g., radiologists, other physicians, and supporting staffs) to render and study remotely located patient data at the locations of their choices.

Another object of the invention is to develop methods and apparatus of teleradiology that allows rendering and studying of remotely located patient volume data without transmitting the entire data to the user's local computer.

Another object of the invention is to develop a secure cost-effective healthcare enterprise-wide solution for data rendering and visualization, and for image data distribution.

Another object of the invention is to provide a solution to further integrate (combine) results from different rendering results, from different rendering methods, from different data sets (regardless of whether they are locally or remotely located), and/or, from different image data acquisition methods.

Another object of the invention is to develop methods and apparatus for data rendering and visualization that efficiently utilizes the high-power computer hardware and/or software at remote locations and alleviates the burden on the network as well as on the user's local computer (hardware and/or software).

Another object of the invention is to develop methods and apparatus that allows software to be centrally installed and managed and to be provided to the user's local computer on an as-needed basis. Furthermore, the software can automatically adjust its configuration based on the user input and/or the configuration of the user's local computer and network.

The teleradiology system of the invention provides a healthcare enterprise-wide solution for rendering and visualization of a remotely located data. It substantially overcomes problems of the prior art as described above. In particular, it is extremely cost-effective, ubiquitously accessible, secure and flexible. The teleradiology system of the invention will improve the accessibility, utilization, and therefore applications, of data (in particular, volume data) rendering and visualization in medicine.

These and further objects and advantages of the invention will become apparent from the ensuing specification, taken together with the accompanying drawings.

DESCRIPTION OF THE DRAWINGS

FIG. 2 is a schematic diagram illustrating principal elements of current (prior art) teleradiology systems.

DETAILED DESCRIPTION OF THE PREFERRED EMBODIMENT

Figure 1:
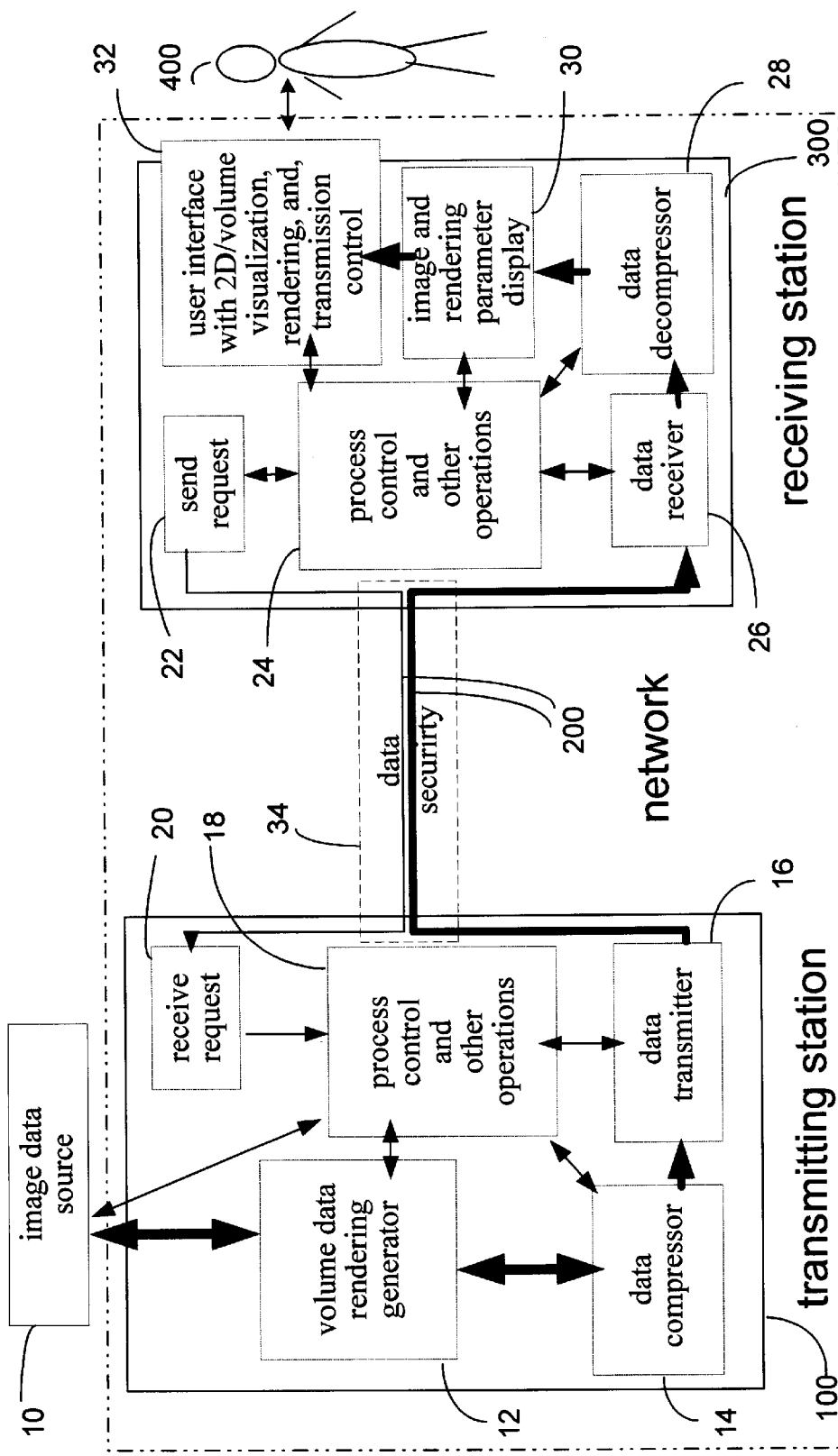
FIG. 1 is a schematic diagram illustrating principal elements of the teleradiology system with remote volume data rendering/visualization capability.

With reference to FIG. 1, the preferred embodiment of the teleradiology system of the invention is comprised of a data transmitting station 100, a receiving station 300, and a network (or a data transmission channel) 200 connecting transmitting station 100 and receiving station 300. A data security (system) 34 extends into transmitting station 100, receiving station 300 and network 200.

Receiving station 300 comprises a data receiver 26, a send request 22, a user interface 32, a data decompressor 28, a display system 30, a central processing system 24, and, data security 34. Transmitting station 100 comprises a data transmitter 16, a receive request 20, a data compressor 14, a volume data rendering generator 12, a central processing system 18, and, data security 34.

Receiving station 300 is controlled by a user 400 and is typically located at the healthcare professional's office or home. Transmitting station 100 is usually located proximate to an image data source 10 (e.g., proximate to image database and/or archiving of a Radiology department). In some cases, image data source 10 may be included in transmitting station 100.

In a preferred operation, user 400 via user interface 32 specifies, one at a time, 1) at least one image data set to be visualized; 2) at least one data rendering method to be used, 3) the rendering parameters used by each rendering method, and 4) the data transmission parameters for controlling data transmission over network 200. Central processing system 24 on receiving station 300 takes and validates the user request. Central processing system 24 then issues the request, which is sent via send request 22 to transmitting station 100 through network 200. Central processing system 18 on transmitting station 100 receive the request via receive request 20. Coordinated by central processing system 18, volume data rendering generator 12 accesses from image data source 10 the image data set which the user has specified, and then generates the data rendering result based on the data rendering method and parameters which the user has specified. The rendering result is usually a 2D image, much smaller in size than the original data set. Data compressor 14 further compresses the result and other parameters based on data transmission parameters which the user has specified. Then, data transmitter 16 on transmitting station 100 transmits the compressed data to data receiver 26 on receiving station 300 via network 200 based on data transmission parameters which the user has specified. On receiving station 300 and coordinated by central processing system 24, data decompressor 28 decompresses (or restores) the rendering result. (The central processing system 24 may also perform further image processing and operations.) Display system 30 displays the result (the image) and other parameters on user interface 32. Via user interface 32, user 400 can further modify 1) the image data set to be visualized, 2) the data rendering method to be used, 3) the rendering parameters used, and 4) the data transmission parameters used. This process goes on until a satisfactory rendering and visualization result is obtained.

With a well-designed teleradiology system, the response time from a user request to the display of the required result is very short and can be ignored or tolerated. Thus, the user can interactively control data rendering as well as transmission, and visualize the rendering result in "real-time". Thus, the user can have virtually the same access to the remotely located volume data that he would have if it were the user's computer.

For comparison, FIG. 2 shows the principal elements of current (prior art) teleradiology systems. The elements in FIG. 2 that correspond to those in FIG. 1 are annotated with the same numbers as in FIG. 1, suffixed by A. The suffix is ignored for network (200), user (400), and image data source (10).

The teleradiology system of the invention (FIG. 1) provides a truly integrated functionality of data transmission of current teleradiology systems and volume data rendering and visualization of current volume data rendering/visualization systems. This integration represents a fundamental change for both teleradiology systems and volume data rendering/visualization systems. For current teleradiology systems, this integration represents a change from the image (2D data) based design to the volume data based design and, consequently, requires special designs in volume data rendering generation (12), rendering display (30), and rendering control (i.e., user interface 32). For current volume data rendering/visualization systems, this integration represents a change from the local dedicated system design to network based system design and, consequently, requires special designs in data transmission (16,26,20,22), data compression (14)/decompression (28), data security (34), and transmission control (i.e., user interface 32). The fundamental change required may explain why this new teleradiology system has not been proposed until now even though both teleradiology systems and volume data rendering/visualization systems have existed for a decade.

Volume Data Rendering and Visualization

Volume data rendering and visualization is a well-established field. There are many volume data rendering/visualization systems for medical applications. The data rendering methods of medical interest include multi-planer reformation, maximum intensity projection, surface rendering, volume rendering, as well as many variations and/or combinations of these methods. The rendering parameters include the viewpoint (i.e., the orientation), the spatial region and the value range (e.g., controlled by thresholds) of the data to be rendered. Volume data rendering in medical applications also relies on image processing tools and data editing tools to select spatial regions of the data set to be rendered (e.g., to exclude the bone structures) and to highlight the structure of interest (e.g., the vascular tree). (For more details on volume data rendering and visualization implementation including software implementation, reference may be made to "The Visualization Toolkit—An Object-Oriented Approach to 3D Graphics", $2_{nd}$ edition, by Will Schroeder, Ken Martin, Bill Lorensen, published by Prentice Hall PTR, 1998.)

Volume data rendering generator and display system

The data rendering methods cited above are usually computationally intensive. They are implemented on volume data rendering generator 12 (FIG. 1). Volume data rendering generator 12 may be implemented on a general-purpose computer, or on a high-performance dedicated computer or computing board (or card, unit) optimized for rendering generation. Similarly, display system 30 on receiving station 300 may be implemented on a general-purpose display system available on typical computers, or on a high-performance dedicated display system. Using high-performance dedicated systems will improve the data rendering and display speed and therefore the response time and the level of interactivity of the teleradiology system. On the other hand, using general-purpose systems will widen the applicability of this system. (U.S. Pat. No. 5,649,173, for example, teaches recent developments regarding graphic computers.) As a preferred tradeoff, volume data rendering generator 12 is implemented on a high-performance dedicated rendering board, while display system 30 is implemented on a general purpose display system available on typical computers.

User interface

User interface 32A of current teleradiology systems (FIG. 2) only allows transmitting and displaying 2D images and other display parameters (e.g., display window parameters). In contrast, user interface 32 of the teleradiology system of the invention (FIG. 1) can, in addition, control rendering and transmission of a volume data set, and display the rendering results and rendering parameters. Note that volume data rendering results are typically in different forms from the original volume image data which these results are generated from. In terms of volume data rendering and visualization, the design and functionality of user interface 32 of the teleradiology system of the invention is similar to that of the current volume data rendering/visualization systems. These design and functionality are well established. (Many vendors' products, e.g., the Advantage Windows product made by General Electric Company, can be used as references.) In particular, user 400 can, via user interface 32, adjust rendering parameters (e.g., viewpoint as well as spatial region and value range of the data to be rendered) and other settings. The techniques for adjusting these parameters and settings include 1) using preset protocols for some typical settings; 2) inputting a specific setting with a keyboard, a mouse and/or other input devices; and/or 3) interactive navigation using a mouse, a trackball, a joystick, a keyboard and/or other navigating devices. In particular, user 400 can, via user interface 32, edit (including process) patient data (e.g., remove the bone structures) in a manner similar to the current volume data rendering/visualization systems. With the teleradiology system of the invention, user 400 can, via user interface 32, define and adjust data rendering methods and parameters, control what is to be rendered, transmitted and visualized next, and eventually obtain the final rendering result. The user interface 32A of current teleradiology systems (FIG. 2) lacks these functionalities of volume data rendering control and display as well as 'on-demand' transmission control.

With the above descriptions on system components, rendering methods, volume data rendering generator, general/ special rendering and display hardware, rendering and visualization software, as well as user interface design and functionality, implementing the volume data rendering and visualization aspects of the teleradiology system of the invention should be clear to one with ordinary skill in the volume data rendering/visualization field.

Data Transmission

Data transmission is a well-established field. Transmission of medical image data over networks has been widely utilized in teleradiology. Many teleradiology systems are currently available. Teleradiology systems require careful consideration in data transmission media (concerning 200) and protocol (concerning 16,26,20,22 and 32), data compression (concerning 14, 28 and 32), data security (34 and 32), integration with image data source and data management (concerning 10 and 32).

Transmission media and protocol

For the teleradiology system of the invention, the preferred transmission media (i.e., network 200) may be an intranet, the internet (including the internet2) or via a direct dial-up using a telephone line with a modem. The preferred data transmission protocol (for components 16, 26, 20, 22) is the standard TCP/IP. Furthermore, for some transmission media (e.g., the internet2), user 400 can control certain aspects (e.g., the priority level, the speed) of data transmission by selecting transmission parameters via user interface 32. These should be well known to one with ordinary skill in the network communication field.

Data compression/decompression

Data compression is a technique for densely packaging the data to be transmitted to efficiently utilize a given bandwidth of network 200 during transmission. This operation is done by data compressor 14 on transmitting station 100. After transmission of compressed data to receiving station 300, data decompressor 28 restores the compressed data in a format ready to be used. The data compressor 14 and decompressor 28 can be implemented either on dedicated processors for improved response speed or on general propose processors for wide applicability. The wavelet compression/decompression—the de facto standard for data compression—is used on the teleradiology system of the invention as a preferred method. (For technical details on data compression in general and wavelet compression in particular, reference may be made to the book "Wavelets and Subband Coding" by Martin Vetterli and Jelena Kovacevic, published by Prentice Hall, 1995.) Specifically, in one embodiment, user 400 can select data compression and transmission parameters via user interface 32. In another embodiment, these selections are done automatically by the teleradiology system based on the system configuration and the data to be transmitted. For example, the compression method selected can be lossless (i.e., the compressed data can be fully restored) or lossy (i.e., the compressed data can only be partially restored). The attainable data compression ratio is about 3:1 for lossless compression and much higher for lossy compression. The data compression ratio represents a tradeoff of preserving image fidelity (with less compression) versus increasing transmission speed (with more compression). Furthermore, transmitted images can also be refined progressively. Due to medical and legal considerations, the teleradiology system of the invention provides lossless and virtually lossless compressions to avoid misdiagnosis. It also provides progressive refinement for improved interactivity. The image compression/ decompression techniques used for the teleradiology system of the invention are similar to that for existing teleradiology systems (i.e., 14A, 28A and 32A in FIG. 2).

Medical image data source and management

The teleradiology system of the invention may be readily integrated with medical image data source 10. In particular, medical image data are stored in the Digital Imaging COmmunications in Medicine (DICOM) standards. (For details on DICOM, refer to Digital Imaging Communication in Medicine, Version 3.1. Rosslyn, Va.: National Electrical Manufacturers Association (NEMA) Standards Publication No. 300–1997, 1997.) DICOM is a hierarchical approach to the storage and communication of medical image data. The patient is the top level of this hierarchy. A patient makes visits to a medical service provider, who performs studies concerning this patient. Studies concerning a given patient are composed of study components (e.g., physician's notes concerning the patient, patient identification information, administrative data) and series. Series are in turn composed of radiological images and other related diagnostic information concerning these images. With appropriate access privileges and via user interface 32, the teleradiology system of the invention is able to search image data source 10 on the basis of a patient, a study, a series, or some combination thereof. It is able to save the studies on receiving station 300 and/or transmitting station 100 for future viewing. Furthermore, it is able to capture the consultation messages. In terms of integration with image data source and patient data management, the teleradiology system of the invention is similar to existing teleradiology systems.

Data security and management

Another medical and legal concern of a teleradiology system is its ability to protect patient privacy and data security. Data security 34 includes the security measures for authentication (i.e., proof of identity), access control, confidentiality, and data integrity. (For detailed technical descriptions on data security, reference may be made to the International Organization for Standardization (ISO) security architecture defined in section 5 of ISO/IEC 7498–2, 1989.) As a minimum requirement for the teleradiology system of the invention, name and password are required to identify the authorized user 400 via user interface 32. Access privileges to the teleradiology system in general and to transmitting station 100 in particular are user specific. An audit trail of system resource usage, patient information access, etc. is provided. Encryption of demographics is employed. Firewalls are installed for Internet connections. Data security measures for the teleradiology system of the invention are similar to that for current teleradiology systems (refer to 34A and 32A in FIG. 2).

With the above descriptions on data compression/ decompression, data security measures, integration with data source and data management, transmission media and protocols, implementing the data transmission aspects of the teleradiology system of the invention should be clear to one with ordinary skill in the field.

New functionalities and capabilities
On-demand rendering/transmission control and Rendering remotely located volume data The teleradiology system of the invention (FIG. 1) integrates the functionality of data transmission of current teleradiology systems and volume data rendering/visualization of current volume data rendering/visualization systems. In comparison, the current two-step approach discussed in the Background of the Invention simply installs an existing teleradiology system (i.e., receiving station 300A in FIG. 2) and an existing volume data rendering/visualization system on one computer. The teleradiology system of the invention, by true integration, provides new functionalities for on-demand rendering and transmission control and new capabilities for rendering and studying remotely located volume data. In comparison, these functionality and capability do not exist in the current two-step approach, i.e., via a simple combination.

With these new functionalities and capabilities, user 400 can navigate through a remotely located volume data set, interactively define and adjust the rendering method and parameters, control what is to be rendered, transmitted and visualized next, and eventually obtain the final rendering result. Thus, user 400 can render and visualize a remotely located volume data set without transmitting the entire volume data set to the user's local computer.

It is to be noted that though medical volume data sets are typically large in size (e.g., 150 MB for a CT Angiography study), in many cases, the user may want to review intermediate and final rendering results only, which are usually much smaller (e.g., of a order of 1 MB) in size. Thus, compared to the current two-step approach, the teleradiology system of the invention greatly alleviates network speed limitations. Furthermore, it eliminates the long initial delay associated with transmitting a large data set over a network, and therefore rendering and visualization can be started almost immediately. It also avoids the problem of generating multiple copies of the data at different locations, which is often desirable for patient data management. With the teleradiology system of the invention, the healthcare providers can further expand the geographic and/or time coverage of their service, resulting in improved healthcare service quality, delivery time, and patient data management, as well as reduced cost.

Different divisions of the rendering generation task

As a preferred embodiment of the invention, the teleradiology system generates the data rendering result exclusively on transmitting station 100, and then transmits the rendering result to receiving station 300. Thus, the hardware (e.g., memory, storage, and computation) demanding operations (e.g., the volume rendering operation) can be performed exclusively on transmitting station 100. This embodiment allows a full utilization of the computer hardware capability at transmitting station 100, and therefore minimizes the hardware requirements on receiving station 300. As a result, users can perform advanced volume data rendering and visualization even with the most basic local computers as receiving stations 300.

In another embodiment of the invention, transmitting station 100 only does a partial computation (e.g., generating a surface rendering model). Central processing system 24 on receiving station 300 completes the remaining part of the computation based on the partial computation done by transmitting station 100, and displays the final rendering result on user interface 32 via display system 30. This embodiment may sometimes further reduce the network load by performing some computations on the user's local computer.

Client-server Software Structure

The teleradiology system of the invention uses client-server design architecture. (For technical details on client-server systems, refer to Dewire DT. *Client/Server Computing*. McGraw-Hill, 1993.) As a result, software of this system can be installed, maintained, and upgraded on one station, referred to as the software server, while the other station is referred to as the software client. In a preferred embodiment, transmitting station 100 acts as the software server and receiving station 300 as the software client. The software for the software client can be supplied by the software server via network 200 at each time of use. Alternatively, it can be installed on the software client once and for future use. In the latter case, the software client is notified, via network 200, when a software upgrade is available. The client-server software implementation greatly reduces the cost of licensing as well as installing, maintaining, and upgrading software on each software client. The system of the invention also can charge the use of the system on either per license basis, per use basis, or other basis.

Web browser based client software

As a preferred embodiment, the software to be run at receiving station 300 is developed based on standard Web browsers (e.g., Microsoft Explorer or Netscape Navigator). Specifically, the software for receiving station 300 can be a "plug-in" of the Web browser, which is installed once and is an integral part of the Web browser on receiving station 300. Alternatively, the software for receiving station 300 can be a Java applet, which is a program sent from transmitting station 100 each time the program is used. (For technical details on Java applet, refer to Horstmann C S, Cornell G. Core Java, Vol 1: Fundamentals. Sun Microsystems, 1998.) Using Web browser based software makes volume data rendering/visualization software available to any authorized user with a networked computer. Using Java based software makes it work on commonly used operation platforms (e.g., Unix and PC).

The client-server implementation and Web browser based implementation make the proposed system very accessible. Any authorized user can perform advanced volume data rendering and visualization tasks from the user's preferred location using a networked computer. As an example, a user can perform advanced volume data rendering and visualization tasks even with the most basic local computers (e.g., the user's desktop computer) and even without the current volume data rendering/visualization software installed on the user's computer.

Interconnection of multiple receiving/transmitting stations

Though only one receiving station 300 and one transmitting station 100 are shown in FIG. 1, multiple receiving stations 300 can be connected to a transmitting station 100 and multiple transmitting stations 100 may be connected to a receiving station 300. Multiple receiving stations 300 can operate individually, i.e., without interfering with each other. Alternatively and as a special mode, some receiving stations may also operate in a collaborative (conference) mode so that the user input at, and the display on, one receiving station can be viewed by multiple receiving stations as a group. Furthermore, multiple computers may be used to collectively serve the function of one transmitting station 100.

Healthcare enterprise-wide image distribution solution for images, information/data repository, and the electronic medical record Because it is extremely cost-effective, ubiquitously accessible, provides acceptable data security protection and data management, and significantly relaxes requirements on network as well as the user's local computer (software and hardware), the teleradiology system of the invention is well suited as a healthcare enterprise-wide image distribution solution. Furthermore, it can serve as an enterprise-wide PACS (Picture Archiving Communication System) and can be readily integrated with other PACS and image distribution systems.

By greatly reducing the cost and drastically improving the accessibility of image distribution, the teleradiology system of the invention is a preferred image distribution method for medical image data, for medical information/data repository, and for the electronic medical record (or computerized patient record). Thus, it may be used in settings where the patient data contains not only image data but also other data (e.g ECG) and information (e.g., notes on patient medical history).

Integration and display of multiple rendering results

The teleradiology system of the invention can be used for rendering and visualizing multiple images resulted from different rendering methods and parameters, from different data sets (regardless of whether they are locally or remotely located), and/or different image data acquisition methods (e.g. CT, MR, US). The rendering methods include volume data rendering as well as conventional 2D image rendering. The multiple displays may be updated individually or simultaneously. For example, images of axial, sagittal and coronal multiplaner reformation containing cursor position may be displayed and updated simultaneously as the cursor moves. Furthermore, maximum intensity projection, volume rendering, and/or, surface rendering results may be individually or simultaneously displayed and/or updated with axial, sagittal and/or coronal images. In addition, results from different studies, be it from one or multiple image data acquisition method, can be individually or simultaneously displayed and/or updated for comparison. The different rendering results from different rendering methods, different rendering parameters, different data sets, and/or different image data acquisition methods can be further combined to form one or multiple composite images.

Operation modes and their selections

The system may have many different operation modes. Examples of different operation modes that have been discussed in previous sections include the different divisions of the rendering generation task between receiving station 300 and transmitting station 100, different data compression/decompression operations with different data compression ratios, different data transmission modes for network 200. In general, the different operation modes also require different software configurations. As exemplified in previous discussions, the different operation modes may be selected either by user 400 via user interface 32, or by one or more automated computer program. Using software configurations as an example, the selection of software configurations can be accomplished with user intervention. Alternatively, software can automatically adjust its configuration based on, for example, the configuration of the teleradiology system (network and transmitting/receiving stations) as well as the data rendering task. For example, if the software detects that receiving station 300 has very basic hardware resources (in terms of memory, storage, and/or computation power) for the data rendering task, it automatically uses the software that performs data rendering exclusively on transmitting station 100.

Other embodiments

Although in a preferred embodiment image data source 10 is accessed via transmitting station 100 and transmitting station 100 also acts as the software server, this invention also includes other embodiments. For example, in one embodiment image data source 10 is accessed via transmitting station 100, but receiving station 300 acts as the software server instead. In this case, transmitting station 100 will use the volume data rendering software provided by receiving station 300 via network 200 to generate the rendering result, partially or completely, on transmitting station 100. In another embodiment, transmitting station 100 acts as the software server, but image data source 10 is located proximate to, and accessed via, receiving station 300 instead. In this case, receiving station 300 will use the volume data rendering/visualization software provided by transmitting station 100 via network 200 to generate, completely on receiving station 300, the rendering result.

Obviously, many other modifications and variations of the present invention are possible in light of the above teachings. It is therefore to be understood that within the scope of the disclosed concept, the invention may be practiced otherwise than as specifically described.

We claim:

1. A post-processing system for remotely accessing patient information and data previously acquired and electronically stored, and for remotely generating a volume data rendering result, comprising:

at least one receiving station controllable by at least one user of said system;

at least one transmitting station physically separated from said receiving station for communicatively coupling to said receiving station through at least one network;

user interface means provided at said receiving station for enabling a user to specify at least one patient volume data set previously acquired and stored in said transmitting station, and to specify at least one request for volume data rendering comprising specifying a volume data rendering method and rendering parameters to be applied on said volume data set;

an image processor at said transmitting station interactively controllable at said receiving station to generate a partial or complete volume data rendering result in real time by processing said volume data set using said volume data rendering method and rendering parameters specified by said user;

a data transmitter provided at said transmitting station for transmitting said processed result to said receiving station; and display means for displaying the requested rendering result and rendering parameters at said receiving station.

2. The system of claim 1 further including:

security and data management means for preventing an unauthorized user from gaining access to said data set from said system.

3. The system of claim 2 wherein:

said security and data management means further include means for employing firewalls during the data transmission and/or for encrypting demographic of said data set.

4. The system of claim 1 further including:

Means included in said transmitting station for compressing data to be transmitted;

means for transmitting said compressed data from said transmitting station to said receiving station through said network; and means included in said receiving station for decompressing said transmitted data.

5. The system of claim 4 wherein:

said compressing means and decompressing means are operable in accordance with each of a plurality of compression/decompression methods, the particular method used being alternatively selected by said user through said user interface, or by an automated computer program.

6. The system of claim 1 wherein:

said receiving station includes means for computing the remaining part of said rendering result.

7. The system of claim 1 wherein:

said system's software is installed, managed and upgraded at one of said stations, the software for the other station being alternatively supplied at each time of use over said network or on a permanent basis.

8. The system of claim 1 further including:

management and software distribution means included in said system for charging the use of said system alternatively on per license basis or on per use basis.

9. The system of claim 1 wherein:

said system has a plurality of operation modes, the particular operation mode used being alternatively selected by said user through said user interface, or by an automated computer program.

10. The system of claim 1 wherein:

said receiving station is provided with software which is usable with a web browser.

11. The system of claim 1 wherein:

said receiving stations comprises one of multiple receiving stations interconnected by said network so that the input and the display at one of said receiving stations can be viewed by other of said receiving stations.

12. The system of claim 1 further including:

data transmission means for transmitting images with progressive refinement.

13. The system of claim 1 wherein:

said user interface means includes image processing tools and data editing tools for editing said data set.

14. The system of claim 1 wherein:

the data transmission is controlled by the transmission parameters, said transmission parameters being alternatively selected by said user through said user interface, or by an automated program.

15. The system of claim 1 wherein:

said user interface means comprises means for enabling said user to specify different data rendering requests resulting from different rendering parameters, different rendering methods, and/or different data sets from one or multiple data acquisition methods, and to specify a method to integrate said different data rendering results into at least one composite rendering result; and said display means for presenting at said receiving station said composite rendering result and a plurality of parameters used for generating said composite rendering result.

16. The system of claim 1, wherein said display means, user interface means and image processor are configured for enabling said user to interactively view said displayed requested rendering result and parameters and specify adjusted volume data rendering methods and parameters to generate updated rendering results.

17. The system of claim 1, wherein said transmitting station and said image processor are couplable to a plurality of receiving stations for serving multiple receiving stations concurrently.

18. The system of claim 1, wherein said transmitting station is implemented with a plurality of computers.

19. A method for locally generating a volume data rendering result in accordance with a remote request for processing of previously acquired and locally stored patient information and data, comprising:

locally storing at least one patient volume data set;

locally receiving an identification of at least one specified patient volume data set and at least one request for volume data rendering from a remote user, the request for volume data rendering comprising a volume data rendering method and rendering parameters to be applied on said specified patient volume data set;

locally generating a partial or complete volume data rendering result in real time by processing said specified patient volume data set using said volume data rendering method and rendering parameters received from said remote user; and locally transmitting said processed result for remotely displaying said requested rendering result and said rendering parameters.

20. The method of claim 19, further comprising:

locally receiving new requests for volume data rendering interactively issued by said remote user based on feedback from said displayed requested rendering result and said rendering parameters, said new requests comprising an adjusted volume data rendering method and adjusted rendering parameters;

locally generating an updated partial or complete volume data rendering result in real time by processing said specified patient volume data set using said adjusted volume data rendering method and adjusted rendering parameters; and repeating said new requests for volume data rendering and said generation of said updated partial or complete volume data rendering result until a desired rendering result is achieved.

* * * * *